(12) United States Patent
Wang et al.

(10) Patent No.: US 11,651,858 B2
(45) Date of Patent: May 16, 2023

(54) PROVIDING MEDICAL TREATMENT USING OPTIMIZED SYMPTOM-CENTRIC DECISION TREES BASED ON DISEASE-CENTRIC KNOWLEDGE GRAPHS

(71) Applicant: INTERNATIONAL BUSINESS MACHINES CORPORATION, Armonk, NY (US)

(72) Inventors: Jian Wang, Beijing (CN); Qi Cheng Li, Beijing (CN); Ya Bin Dang, Beijing (CN); Li Jun Mei, Beijing (CN); Xin Zhou, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 557 days.

(21) Appl. No.: 16/056,832

(22) Filed: Aug. 7, 2018

(65) Prior Publication Data
US 2020/0051692 A1 Feb. 13, 2020

(51) Int. Cl.
*G16H 50/20* (2018.01)
*G16H 10/60* (2018.01)
*G16H 50/30* (2018.01)

(52) U.S. Cl.
CPC .............. *G16H 50/20* (2018.01); *G16H 10/60* (2018.01); *G16H 50/30* (2018.01)

(58) Field of Classification Search
CPC ........ G16H 50/00; G16H 50/20; G16H 50/30; G16H 50/50; G16H 50/70; G16H 50/80; G16H 10/60
See application file for complete search history.

(56) References Cited

U.S. PATENT DOCUMENTS

| 5,544,651 | A  | * | 8/1996  | Wilk           | G16H 40/67 |
|           |    |   |         |                | 600/310    |
| 7,344,496 | B2 |   | 3/2008  | Iliff          |            |
| 2004/0044546 | A1 | * | 3/2004 | Moore         | G16H 50/20 |
|           |    |   |         |                | 705/2      |
| 2012/0301864 | A1 | * | 11/2012 | Bagchi       | A61B 5/00  |
|           |    |   |         |                | 434/362    |
| 2017/0277840 | A1 |  | 9/2017  | De La Torre et al. | |
| 2018/0011979 | A1 | * | 1/2018 | Zhong         | G16H 50/20 |
| 2018/0122509 | A1 | * | 5/2018 | Christiansson | G16H 40/63 |
| 2018/0218126 | A1 | * | 8/2018 | Salazar       | G16H 50/30 |

(Continued)

FOREIGN PATENT DOCUMENTS

EP          3032472          6/2016

OTHER PUBLICATIONS

Travis R. Goodwin et al., Medical Question Answering for Clinical Decision Support, Proc ACM Int Conf Inf Knowl Manag. Author manuscript; available in PMC Jul. 27, 2017.

(Continued)

*Primary Examiner* — Pamela M. Bays
(74) *Attorney, Agent, or Firm* — Tutunjian & Bitetto, P.C.; Joseph Petrokaitis (57) ABSTRACT

Methods and systems for treating a disease include navigating a symptom-centric decision tree which accounts for probabilities for symptoms and diseases and emergency values for the symptoms and diseases, based on information provided by a user, to determine a disease. A treatment is provided to the user based on the determined disease.

19 Claims, 5 Drawing Sheets

(56) References Cited

U.S. PATENT DOCUMENTS

2019/0192768 A1\* 6/2019 Gupta ............... A61M 5/14276
2019/0286661 A1\* 9/2019 O'Connor .............. G06N 20/00

OTHER PUBLICATIONS

Jingchi Jiang et al., Learning and inference in knowledge-based probabilistic model for medical diagnosis, Computer Science > Artificial Intelligence, Mar. 28, 2017.
Maya Rotmensch et al., Learning a Health Knowledge Graph from Electronic Medical Records, Scientific Repods, Jul. 20, 2017.

\* cited by examiner

PROVIDING MEDICAL TREATMENT USING OPTIMIZED SYMPTOM-CENTRIC DECISION TREES BASED ON DISEASE-CENTRIC KNOWLEDGE GRAPHS

BACKGROUND

Technical Field

The present invention generally relates to conversation-based diagnosis and treatment and, more particularly, to using symptom-centric decision trees that include priority information.

Description of the Related Art

Conversation-based disease inquiry and diagnosis enables rapid and intuitive self-diagnosis and/or medical intake, triage, and treatment. A user receives a series of questions, with each question being selected to determine information relevant to diagnosis. The users' answers to the questions, which can frequently be provided in the form of natural language responses, are then used to determine what symptoms the user exhibits and, thus, what disease or diseases underlie those symptoms.

SUMMARY

A method for treating a disease includes navigating a symptom-centric decision tree which accounts for probabilities for symptoms and diseases and emergency values for the symptoms and diseases, based on information provided by a user, to determine a disease. A treatment is provided to the user based on the determined disease.

A system for treating a disease includes a decision tree module configured to navigate a symptom-centric decision tree which accounts for probabilities for symptoms and diseases and emergency values for the symptoms and diseases, based on information provided by a user, to determine a disease. A treatment module is configured to providing a treatment to the user based on the determined disease.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Embodiments of the present invention provide automatic patient diagnosis and treatment by, e.g., conversation-based inquiry that uses an optimized, symptom-centric decision tree that may be derived from a disease-centric knowledge base. The present embodiments derive the symptom-centric decision tree by considering not only a probability that a given symptom is associated with a particular disease, but also a "priority" or "emergency" score for symptoms and diseases.

The present embodiments also provide classification of diseases along treatment lines, with multiple diseases having the same treatment being grouped together. Thus the diagnosis conversation need not identify a specific disease from a group of similar diseases, when those diseases share a treatment. This saves time and potential frustration on the part of the user, as the conversation reaches a conclusion quickly, without delving into unnecessary detail.

A disease-centric knowledge base maintains a graph of relationships between symptoms, sub-diseases, and diseases. The knowledge graph includes directed edges, whereby a symptom implies a sub-disease or disease. A set of n diseases is represented as $D=\{d_i | i \in [1, \ldots, n]\}$. The diseases may have a hierarchical structure, with particular disease at the top of the hierarchy and with sub-diseases representing sub-types of the disease or phases of the disease. Thus, each disease $d_i$ may have a set of $m_i$ sub-diseases, defined as $sd_i=\{sd_{ij} | j \in [1, \ldots, m_i]\}$.

Symptoms can be understood as an observation of the user's condition. Symptoms may therefore include physical observations and behavioral observations that show some deviation from the user's healthy condition. The set of l symptoms is expressed herein as $S=\{s_k k \in [1, \ldots, l]\}$. Symptoms can be grouped into "manifestations," which include multiple symptoms with a logical "AND" relation, such that each of the multiple symptoms is needed to indicate the manifestation. A disease can have multiple manifestations, and if any manifestation m of the disease is present, then that indicates the possibility of the disease, with the probability depending on the probability weight between the disease and the manifestation. If a manifestation can be confirmed directly, then that implies that all of its component symptoms are present. The inclusion of manifestations in the disease-centric knowledge graph addresses the logical connection between certain symptoms with respect to certain diseases.

Manifestations can thus be seen as special symptoms or super-symptoms, grouping symptoms together under one recognizable umbrella. Manifestations may represent multiple specific symptoms at a high level of abstraction, for example aggregating the symptoms of fatigue, fever, muscle aches, and headaches as the manifestation of "flu-like symptoms," though a manifestation need not have a common name.

Each disease $d_i$ is associated with one or more treatments, which are expressed herein as $T=\{t_i | i \in [1, \ldots n]\}$. Diseases can be aggregated according having the same treatments. Thus, without identifying the specific disease, an effective treatment can be administered. Following the example of influenza, the disease known as "the flu" actually represents a set of related viruses. If the treatments for all varieties of influenza are similar, then the conversation need not attempt to identify which sub-type is involved.

Figure 1:
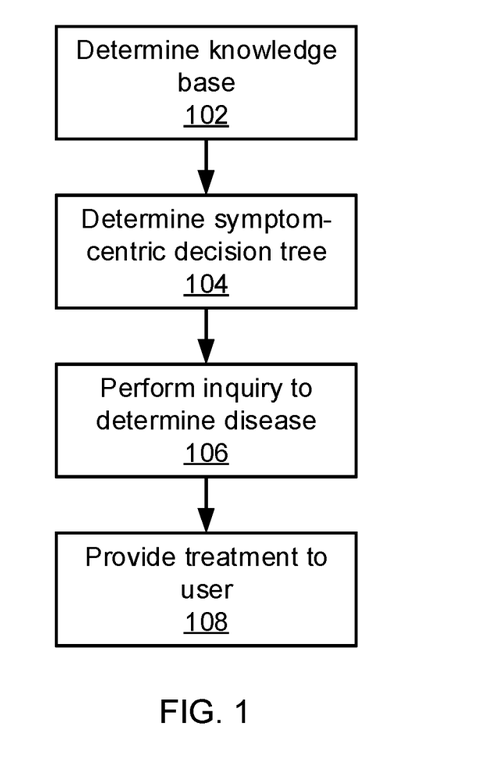
FIG. 1 is a block/flow diagram of a method for providing treatment to a user following a conversation-based inquiry that is guided by a symptom-centric decision tree that includes emergency information for symptoms and diseases in accordance with an embodiment of the present invention.

Referring now to FIG. 1, a method of diagnosis and treatment is shown. Block 102 determines a disease-centric knowledge base that includes relationships between symptoms and diseases. The relationships may be represented as directed edges in a graph that connect a symptom to a disease or sub-disease or connect a sub-disease to another sub-disease or disease. Each edge carries an "implies" relation, where confirming the presence of a symptom of a source node provides a certain probability that the sub-disease or disease of the target node is present. Each symptom and disease may also have an associated "emergency" value that indicates a level of urgency or severity of that symptom or disease. Each graph may be hierarchically organized, with a particular disease being represented by a root node and having one or more levels of sub-diseases before reaching leaf nodes that represent symptoms.

The knowledge base may be represented by a table that captures the relationships between symptoms and diseases. Thus, an exemplary decision tree table in a knowledge base with M disease and N symptoms might look like Table 1 below:

TABLE 1

| Symptom 1 | ... | Symptom N | Disease |
|---|---|---|---|
| 0 | ... | 1 | Disease 1 |
| 1 | ... | 1 | Disease 2 |
| ... | ... | ... | ... |
| 0 | ... | 0 | Disease M |

In this example, the entries of the table are binary-valued, where a "1" indicates that the symptom is related to the disease and a "0" indicates that the symptom is not related to the disease. However, in realistic scenarios these values may be any number between 0 and 1, representing a probability value that the disease in question is indicated by a symptom. In particular, this value captures both the probability of occurrence and the "emergency" value, such that more urgent symptoms and diseases will be weighted more heavily.

For diseases that have the same treatment, the diseases can be grouped by adding a "new" disease that identifies the shared treatment. Thus, symptoms that indicate any of the diseases in the group will point to the treatment that applies to all of the associated diseases. The relationship between diseases and sub-diseases can similarly be captured by listing all of the symptoms of child-disease as being associated with the parent-disease.

Block 104 then determines a symptom-centric decision tree. The decision tree is represented as a directed graph, with each node representing a set of possible outcomes and each outgoing edge representing one decision that may be made at that node to further narrow the possible outcomes. Records may be extracted from the knowledge base table as $(x, Y) = s_1, s_2, s_3, \ldots, s_k, d_i)$.

Based on the entries of the decision graph table, the features $X_i$, of the decision tree (dealing with the symptoms associated with disease i) and the variables $Y_i$ of the decision tree (dealing with the disease i itself) are used to build the decision tree by any appropriate process. These values may be calculated as $X_i = f(e(s_i), g(s_i))$ and $Y_i = f(e(d_i), g(d_i))$, where the function $f$ represents, for example, a linear combination of $e(\bullet)$ and $g(\bullet)$ weighted by respective empirical weight values $w_1$ and $w_2$ as $f(a,b) = w_1 a + w_2 b$. The function $e(\bullet)$ represents an emergency value of the symptom or disease while the function $g(\bullet)$ represents a probability for the symptom or disease. The "emergency" and "probability" values are set according to domain knowledge relating to the disease and symptoms at issue. High "emergency" and "probability" values will effectively raise the priority of a particular path in the decision tree.

For example, following the iterative dichotomiser 3 (ID3) process for generating a decision tree, an entropy and an information gain are calculated using the records extracted from the knowledge base table. However, rather than simply using the number of diseases identified by particular symptoms, the present embodiments use the values of $X_i$ and $Y_i$ defined above. For example, ID3 defines entropy of a set of diseases S as:

$$H(S) = \sum_{y \in Y} -p(y) \log_2 p(x)$$

where y is a class of disease, Y is the set of diseases, and p(y) is the sum of disease weights $Y_i$ for a portion of the diseases in class y divided by the sum of disease weights $Y_i$ for all diseases. The information gain by identifying a particular symptom A is similarly defined as:

$$IG(A, S) = H(S) - \sum_{t \in T} p(t) H(t)$$

where T is a set of subsets of S that are split by whether they are associated with the symptom A, p(t) for subsets that include A is the symptom A's weight according to the definition of $X_i$ above multiplied by the sum of the disease weights $Y_i$ in the subset t divided by the sum of the disease weights $Y_i$ for all diseases, and p(t) for subsets that do not include A is $(1-X_i)$ multiplied by the sum of the disease weights $Y_i$ in the subset t divided by the sum of the disease weights $Y_i$ for all diseases.

In this manner, the existing process for converting data into a decision tree is used with a new definition for the p function, and this new definition can be used for any appropriate decision tree learning process that is appropriate for the particular application at hand.

In some embodiments, block 104 may determine multiple different decision trees, representing early, middle, and late stages for the diseases in question based on corresponding early, middle, and late stage entries for the disease in the knowledge base.

Block 106 then performs an inquiry with the user to determine a disease. The inquiry may, for example, include a conversation-based interaction. The inquiry may therefore include a set of questions that establish a path through the decision tree to a particular disease or group of diseases. An exemplary series of questions and responses are provided below in Table 2.

TABLE 2

| Question | Response |
|---|---|
| What symptom is troubling you the most? | Headache |
| How long has this been troubling you? | Two days |
| Is the headache mainly on one side, or both sides? | Both sides |
| How does bending forward affect the headache? | Worsens |

TABLE 2-continued

| Question | Response |
| --- | --- |
| Have you recently spent time in direct sunlight, experienced hot weather conditions, or used a tanning bed? | No |
| Did you suffer a head injury before your first symptom occurred? | No |
| Do you have pain or pressure in your sinuses? | No |
| Is your scalp sore when touched or pressed? | Yes |
| ... | ... |
| How are your symptoms changing over time? | They are staying about the same |

This inquiry navigates through the decision tree, with each response providing the next edge to take. Ultimately the path through the decision tree will reach a leaf node, indicating a disease diagnosis. Block 108 determines an appropriate treatment t associated with the diagnosed disease $d_i$, and provides that treatment to the user. Treatment may include, for example, administering an injection, providing a medication for self-administration, altering a treatment regimen, and providing instructions to caregivers regarding treatment activities.

Figure 2:
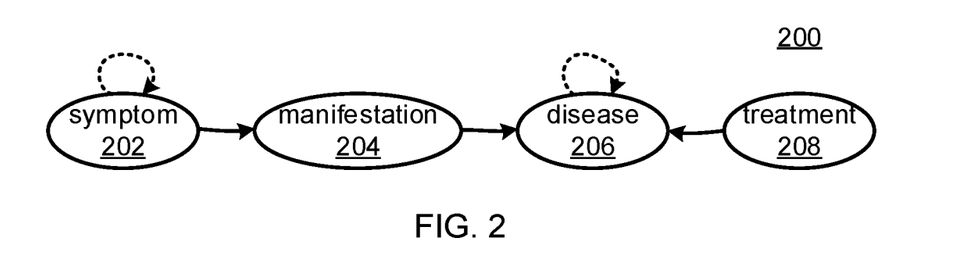
FIG. 2 is a diagram of a knowledge base graph model that illustrates potential relationships between symptoms, manifestations, diseases, and treatments in accordance with an embodiment of the present invention.

Referring now to FIG. 2, an exemplary model 200 of a knowledge graph is shown, illustrating the relations between different types of nodes. A symptom 202 implies a particular manifestation 204. Symptoms 202 may also be related to other symptoms 202 in a hierarchical fashion, where one symptom 204 may be a specific kind of a more general symptom 204. Each manifestation 204 implies a particular disease 206. The disease 206 may also be related to other diseases 206 in a hierarchical fashion, where one disease 206 may be a specific kind of a more general disease 206. A treatment 208 applies to a disease 206. A dotted line indicates a relation of, "is a kind of," showing that a symptom or a disease may have a hierarchical relationship with another symptom or disease as described above.

Figure 3:
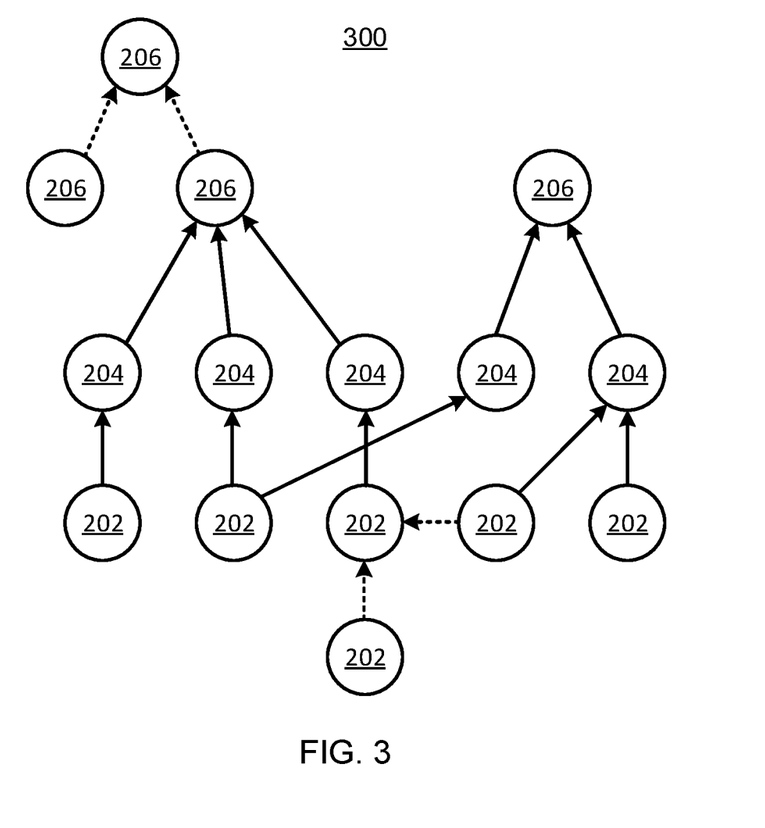
FIG. 3 is a diagram of an exemplary knowledge base graph that illustrates a set of related symptoms, manifestations, and diseases in accordance with an embodiment of the present invention.

Referring now to FIG. 3, an exemplary knowledge graph 300 is shown, illustrating how different manifestations 204 aggregate sets of symptoms 202 as well as the hierarchical relationships between respective sets of diseases 206 and symptoms 202. For example, one disease 206 might be influenza and another disease 206 might be common cold, both of which are types of the more general disease 206 of an upper respiratory infection. A manifestation 204 is also shown with two associated symptoms 202, where all associated symptoms 202 need to be present for the manifestation 204 to be recognized, essentially establishing a Boolean "AND" condition. Some diseases 206 and symptoms 202 have a higher health risk than others. During diagnosis, these high-risk diseases 206 and symptoms 202 should be considered first, to give sufficient time for treatment. These high-risk diseases 206 and symptoms 202 are assigned a higher "emergency" value and are given greater priority during the inquiry of block 106.

As noted above, knowledge graphs are built on a per-disease basis. During the inquiry of block 106, however the questions are symptom-oriented and need to be asked in such a manner as to quickly and effectively narrow down the possible diseases. With each question that is asked, the number of suspected diseases is reduced until the decision tree arrives at a treatment solution. The process of block 106 may begin with some information, for example one or more principal symptoms that help identify a type of disease at a high level (e.g., muscular symptoms, respiratory symptoms, etc.).

Figure 4:
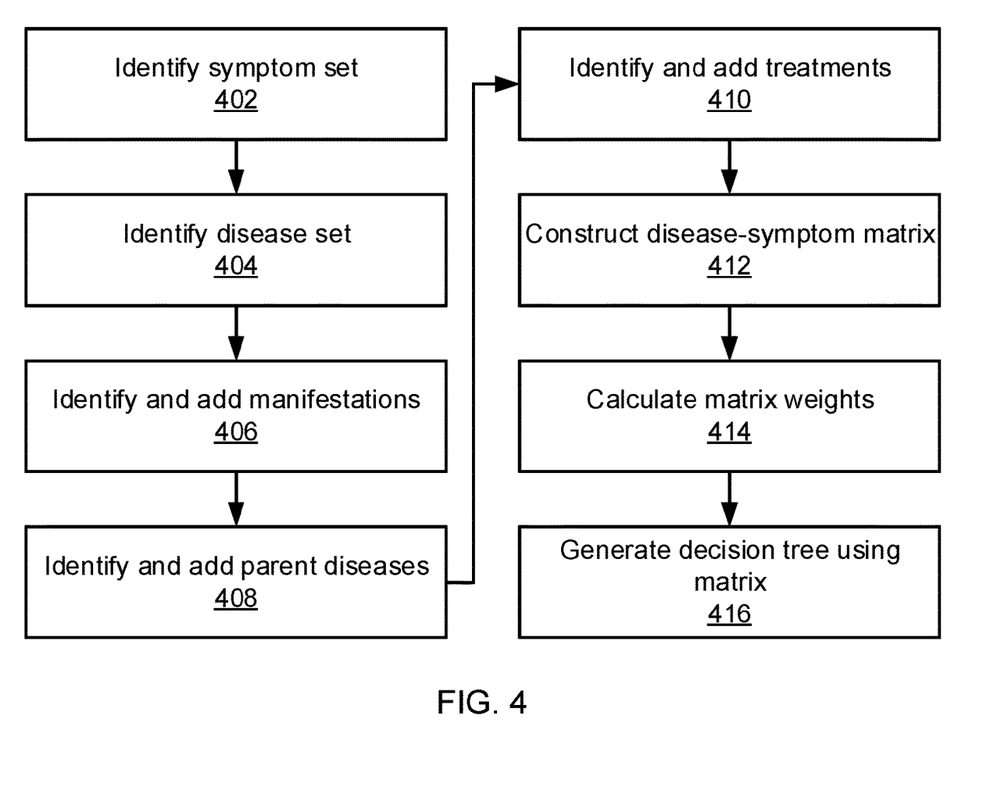
FIG. 4 is a block/flow diagram of a method for generating a symptom-centric decision tree from a disease-centric knowledge base in accordance with an embodiment of the present invention.

Referring now to FIG. 4, additional detail is provided on the determination of the symptom-centric decision tree in block 104. Block 402 identifies the symptom set from the knowledge graph and block 404 identifies the disease set. The symptom set can be identified as $X_1$ and the disease set can be identified as $Y_i$. Block 406 then seeks to identify manifestations from the knowledge graph, for example identifying symptoms that always co-occur for particular diseases. Block 406 represents these manifestations as symptoms of their own. Block 408 then identifies the relationships between diseases, with multiple related diseases having an associated "parent" or general type that includes all of the related diseases. This parent-disease is represented as its own distinct disease, having associated with it the symptoms that are common to all of its child-diseases. Block 410 identifies treatments for diseases and groups of diseases, adding these as if they were diseases unto themselves, with associated symptoms that indicate the treatment.

Block 412 uses this information to construct a disease-symptom matrix, with each row representing a "disease" (including the diseases themselves, parent diseases, and treatments) and each column representing a "symptom" (including the symptoms themselves as well as manifestations that represent multiple symptoms and an "AND" relation). Block 414 calculates the matrix weights, with particular values for each symptom in relation to each disease being set according to a combination of a probability value and an emergency value, as described above. Block 416 then converts the matrix into a decision tree using any appropriate decision tree learning process. The resulting decision tree will encode not only the predictive weight of particular symptoms with respect to each disease (represented by the "probability" value) but will also encode the potential severity of a symptom or disease. As a result, the decision tree will tend toward identifying more severe diseases so that treatment can begin sooner (e.g., without eliminating less severe diseases first).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 5:
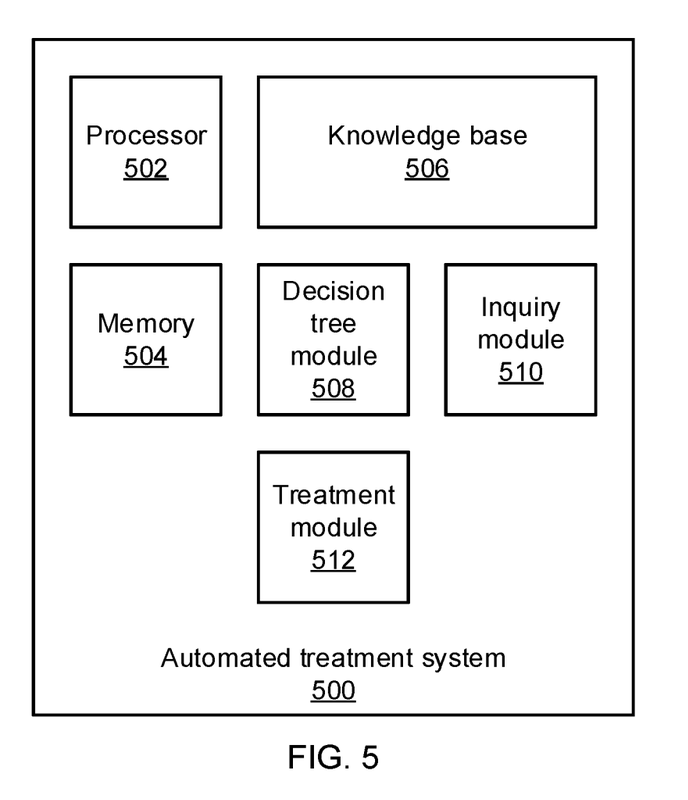
FIG. 5 is a system for providing treatment to a user in accordance with an embodiment of the present invention.

Referring now to FIG. 5, an automated treatment system 500 is shown. The system 500 includes a hardware processor 502 and memory 504. The memory 504 stores a knowledge base 506 that includes a disease-centric knowledge graph as described above, establishing associations between symptoms and diseases. The system 500 includes one or more functional modules that may be implemented as software that is stored in memory 504 and that is executed by processor 502. In other embodiments, the functional modules may be implemented as one or more discrete hardware components in the form of, e.g., application-specific integrated chips or field programmable gate arrays.

A decision tree module 508 processes the information in the knowledge base 506 to create a diagnosis decision tree. The decision tree module 508 further refines the information of the knowledge base 506 to establish certain structural correspondences between, e.g., symptoms and diseases by creating additional entries for manifestations, parent-diseases, and treatments. An inquiry module 510 then uses the decision tree to guide a conversation-based inquiry with a user or patient. The inquiry module 510 presents the user with a series of questions through an appropriate user interface. The answers to those questions guide the decision tree module 508 through the decision tree until a final classification has been reached, determining a disease and/or treatment appropriate to the user.

Treatment module 512 then administers a treatment to the user. In some embodiments the treatment may be performed automatically. For example, the treatment module 512 may trigger the release of medicine through an intravenous route or may provide an injection. In other embodiments, the treatment module 512 may direct the user or a care provider as to the appropriate treatment for the patient. The treatment module 512 prioritizes potential treatments that have a high level of "emergency" associated with the disease being treated.

Figure 6:
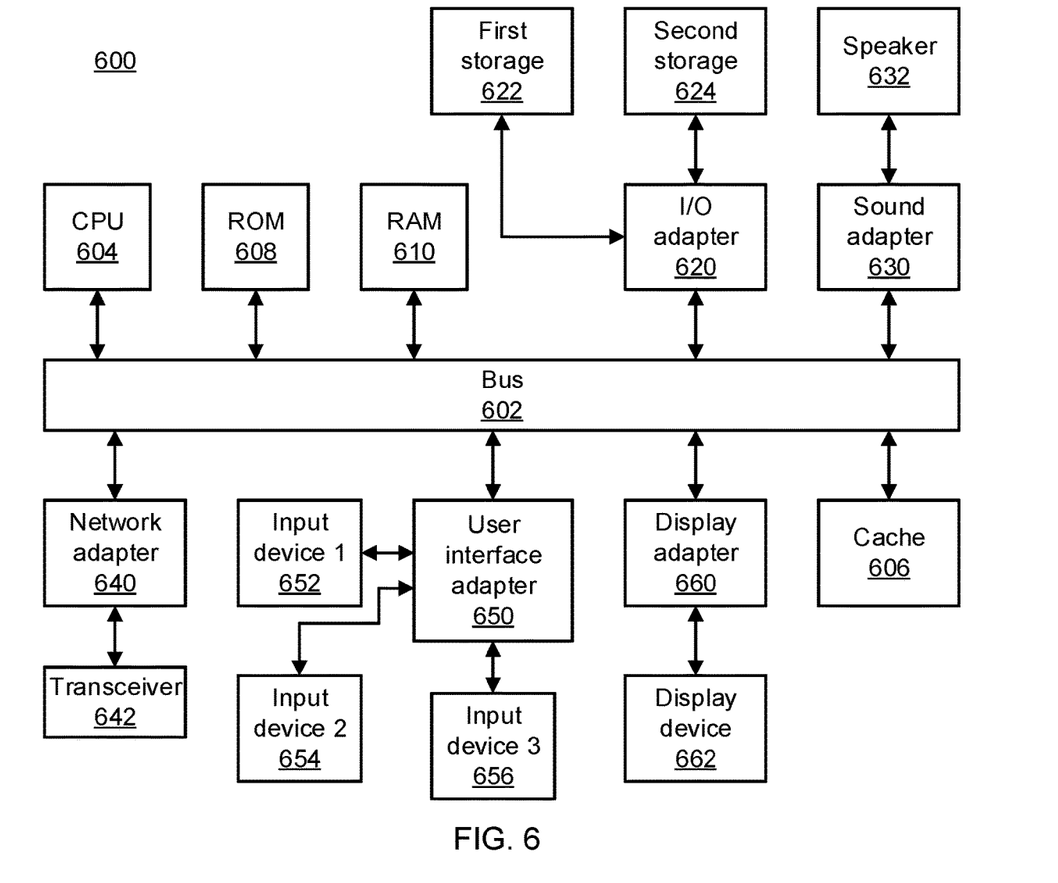
FIG. 6 is a block diagram of a processing system in accordance with an embodiment of the present invention.

Referring now to FIG. 6, an exemplary processing system 600 is shown which may represent the automated treatment system 500. The processing system 600 includes at least one processor (CPU) 604 operatively coupled to other components via a system bus 602. A cache 606, a Read Only Memory (ROM) 608, a Random Access Memory (RAM) 610, an input/output (I/O) adapter 620, a sound adapter 630, a network adapter 640, a user interface adapter 650, and a display adapter 660, are operatively coupled to the system bus 602.

A first storage device 622 and a second storage device 624 are operatively coupled to system bus 602 by the I/O adapter 620. The storage devices 622 and 624 can be any of a disk storage device (e.g., a magnetic or optical disk storage device), a solid state magnetic device, and so forth. The storage devices 622 and 624 can be the same type of storage device or different types of storage devices.

A speaker 632 is operatively coupled to system bus 602 by the sound adapter 630. A transceiver 642 is operatively coupled to system bus 602 by network adapter 640. A display device 662 is operatively coupled to system bus 602 by display adapter 660.

A first user input device 652, a second user input device 654, and a third user input device 656 are operatively coupled to system bus 602 by user interface adapter 650. The user input devices 652, 654, and 656 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 652, 654, and 656 can be the same type of user input device or different types of user input devices. The user input devices 652, 654, and 656 are used to input and output information to and from system 600.

Of course, the processing system 600 may also include other elements (not shown), as readily contemplated by one of skill in the art, as well as omit certain elements. For example, various other input devices and/or output devices can be included in processing system 600, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 600 are readily contemplated by one of ordinary skill in the art given the teachings of the present principles provided herein.

Having described preferred embodiments of providing medical treatment using optimized symptom-centric decision trees based on disease-centric knowledge graphs (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for treating a disease, comprising;
building a symptom-centric decision tree using program code that is executed by a hardware processor and that causes the hardware processor to create a new symptom-centric decision tree based on a disease-centric knowledge base graph, where the symptom-centric decision tree accounts for probability values for symptoms and diseases and emergency values for the symptoms and diseases;
navigating the symptom-centric decision tree based on information provided by a user, to determine a disease;
determining a treatment for the user, based on the determined disease, using the symptom-centric decision tree; and
providing the treatment to the user based on the determined disease, ding triggering release of medicine through an intravenous route or by injection.

2. The method of claim 1, further wherein building the symptom-centric decision tree from the disease-centric knowledge base graph uses a combination of the probability values and the emergency values to determine features and variables of the symptom-centric decision tree.

3. The method of claim 2, further comprising refining the disease-centric knowledge base graph to capture structural relationships between symptoms and between diseases before building the symptom-centric decision tree.

4. The method of claim 3, wherein refining the disease-centric knowledge base graph comprises introducing a manifestation that consists of a plurality of symptoms of the disease-centric knowledge base graph that co-occur in association with a disease of the disease-centric knowledge-base graph with a logical "AND" relation.

5. The method of claim 3, wherein refining the disease-centric knowledge base graph comprises introducing a treatment that is associated with a plurality of symptoms of the disease-centric knowledge base graph that identify a plurality of diseases of the disease-centric knowledge base graph.

6. The method of claim 3, wherein refining the disease-centric knowledge base graph comprises introducing a parent-disease that is associated with a plurality of child-diseases and that is associated with a set of symptoms that is a union of sets of symptoms associated with each of the plurality of child-diseases.

7. The method of claim 2, wherein building the symptom-centric decision tree comprises determining symptom and disease weights based on the probability values and the emergency values.

8. The method of claim 7, wherein each symptom and disease weight is a linear combination of a respective probability value and emergency value.

9. The method of claim 2, wherein building the symptom-centric decision tree includes building respective decision trees for early, middle, and late stages of diseases.

10. The method of claim 1, wherein navigating the symptom-centric decision tree comprises performing a conversational inquiry that presents the user with questions corresponding to symptom information at nodes of the symptom-centric decision tree and records responsive information provided by the user.

11. A non-transitory computer readable storage medium comprising a computer readable program for treating a disease, wherein the computer readable program when executed on a computer causes the computer to perform the steps of:
creating a new symptom-centric decision tree, which accounts for probability values for symptoms and diseases and emergency values for the symptoms and diseases, based on a disease-centric knowledge base graph;
navigating the symptom-centric decision tree, using a processor, based on information provided by a user, to determine a disease;
determining a treatment for the user, based on the determined disease, using the symptom-centric decision tree; and
providing the treatment to the user based on the determined disease, including, triggering release of medicine through an intravenous route or by injection.

12. A system for treating a disease, comprising:
a hardware processor; and
a memory, storing computer program code that, when executed by the hardware processor, implements:
decision tree code that creates a symptom-centric decision tree, which accounts for probability values for symptoms and diseases and emergency values for the symptoms and diseases, based on a disease-centric knowledge base graph, and navigates the symptom-centric decision tree, based on information provided by a user, to determine a disease, and,
treatment code that determines a treatment for the user, based on the determined disease, using the symptom-centric decision tree, and that automatically triggers the administration of the treatment to the user based on the determined disease, including triggering release of medicine through an intravenous route or by injection.

13. The system of claim 12, wherein the decision tree code further builds the symptom-centric decision tree from the disease-centric knowledge base graph, using a combination of the probability values and the emergency values to determine features and variables of the symptom-centric decision tree.

14. The system of claim 13, wherein the decision tree code further refines the disease-centric knowledge base graph to capture structural relationships between symptoms and between diseases before building the symptom-centric decision tree.

15. The system of claim 14, wherein the decision tree code further introduces a manifestation to the disease-centric knowledge base graph that consists of a plurality of symptoms of the disease-centric knowledge base graph that co-occur in association with a disease of the disease-centric knowledge-base graph with a logical "AND" relation.

16. The system of claim 14, wherein the decision tree code further introduces a treatment to the disease-centric knowledge base graph that is associated with a plurality of symptoms of the disease-centric knowledge base graph that identify a plurality of diseases of the disease-centric knowledge base graph.

17. The system of claim 14, wherein the decision tree code further introduces a parent-disease to the disease-centric knowledge base graph that is associated with a plurality of child-diseases and that is associated with a set of symptoms that is a union of sets of symptoms associated with each of the plurality of child-diseases.

18. The system of claim 13, wherein the decision tree code further builds respective decision trees for early, middle, and late stages of diseases.

19. The system of claim 13, wherein the decision tree code further determines symptom and disease weights based on the probability values and the emergency values as a linear combination of respective probability values and emergency values.

* * * * *